United States Patent [19]

Barthelmes et al.

[11] Patent Number: 5,165,106
[45] Date of Patent: Nov. 17, 1992

[54] CONTOUR COLLIMATOR

[75] Inventors: Norbert Barthelmes, Erlangen, Fed. Rep. of Germany; Rafael Nita, San Rafael, Calif.

[73] Assignee: Siemens Medical Laboratories, Inc., Concord, Calif.

[21] Appl. No.: 711,233

[22] Filed: Jun. 6, 1991

[51] Int. Cl.[5] .............................................. H01J 37/09
[52] U.S. Cl. ................................. 250/505.1; 378/150
[58] Field of Search .................... 250/505.1; 378/148, 378/150, 153

[56] References Cited

U.S. PATENT DOCUMENTS

| 4,027,167 | 5/1977  | Pollermann      | 378/153   |
| 4,055,770 | 10/1977 | Milcamps et al. | 250/505.1 |
| 4,121,109 | 10/1978 | Taumann et al.  | 250/505   |
| 4,140,129 | 2/1979  | Heinz et al.    | 250/505.1 |
| 4,220,866 | 9/1980  | Taumann et al.  | 250/513   |
| 4,324,979 | 4/1982  | Bewley et al.   | 250/505.1 |
| 4,450,578 | 5/1984  | Hill            | 378/152   |
| 4,463,266 | 7/1984  | Brahme          | 250/505.1 |
| 4,794,629 | 12/1988 | Pastyr et al.   | 378/150   |

FOREIGN PATENT DOCUMENTS 0245768  11/1990  European Pat. Off. .

Primary Examiner—Bruce C. Anderson
Attorney, Agent, or Firm—Lawrence C. Edelman

[57] ABSTRACT

In a contour collimator for radiation therapy, a variable aperture is formed by two stacks of aperture plates, which are mounted opposite one another. The aperture plates are connected to a setting mechanism in order to alter the aperture created between the opposed aperture plates. All the aperture plates of each stack are arranged on a respective axle. The aperture plates can be rotated individually around the axles and into the aperture.

13 Claims, 3 Drawing Sheets

CONTOUR COLLIMATOR

BACKGROUND OF THE INVENTION

1. Field of the Invention

The invention relates to a contour collimator having a variable aperture.

2. Description of the Prior Art

Contour collimators having a variable aperture are used, e.g. in radiation therapy, because malignant tissue is destroyed by exposing it to a powerful gamma (photon) or electron radiation beam. At the same time, it is important that healthy tissue not be damaged. For this purpose, in radiation therapy equipment a contour collimator is placed between the source of radiation and the irradiated area, for limiting the radiation to essentially the malignant tissue.

A very common practice is to use contour collimators that consist of four aperture plates arranged at right angles to one another and which can be shifted with respect to one another. Thus, with collimators of this kind, only a rectangular radiation field can be produced. On the other hand, the malignant tissue usually has an irregular shape, so that healthy tissue may also be irradiated by the therapy.

In many oncological problem situations, better therapeutic results can be achieved if the distribution of the radiation dose is adapted to the, usually irregular, shape of the tumors. For this purpose, irregularly shaped auxiliary collimators are often constructed individually for the patients in radiation therapy. With the aid of patterns based on X-ray images, irregular field shapes are cut out of rigid foam boards, and these are cast with metal alloys having a low melting point. Thus, for every patient one or more cast collimators must be prepared. The disadvantages of these kinds of collimators are the expensive manufacturing process and the large amount of space required for storage.

A contour collimator of the above-mentioned kind, having an adjustable aperture, is known from EP-A-0 245 768. To make it adjustable, two stacks of aperture plates, which can be shifted with respect to one another, are mounted opposite one another. The lateral surfaces of the aperture plates in the stacks, which can be introduced into the aperture, are oriented toward the midpoint of the source of radiation. Collimators of this kind are also referred to as focused collimators. By this means, it is ensured that the radiation emitted from the midpoint of the radiation source always hits the same absorption cross-section. However, the construction of a focused collimator is expensive because the aperture plates must assume different angles, depending on how far they are inserted into the aperture. This requires an appropriate guide system for the aperture plates. In addition, further steps must be taken to prevent scatter radiation from reaching healthy tissue through the slits that are aligned with the source of radiation.

SUMMARY OF THE INVENTION

1. Objects

It is an object of the invention to provide a simply constructed contour collimator for radiation therapy having a simple construction, and wherein the aperture formed by the aperture plates can be easily adjusted to the outlines of the malignant tissue.

2. Summary

In accordance with the invention there is provided a contour collimator which comprises two stacks of aperture plates which are rotatably mounted opposite to one another on respective axles in a support means and which are creating an aperture between the opposing aperture plates. A setting mechanism is operatively connected to the aperture plates for individually rotating respective ones of the aperture plates about the axles and thereby altering the aperture created by the aperture plates.

Expensive guide systems to orient the aperture plates to the midpoint of the radiation source (focusing) are no longer necessary, but the aperture can nevertheless be adapted in its outline or its contour to the outline of the malignant tissue.

An advantageous embodiment of the invention is distinguished by the fact that each aperture plate is given an elongated shape, bounded by two long sides and a first and second short side, and that a hole is bored in the vicinity of the first short side, which serves to receive the axle. This makes it possible to form the outline of large apertures.

Another advantageous design is distinguished by the fact that each aperture plate is of uniform thickness and that the number of aperture plates in the two stacks is odd. In this embodiment, there are no slits in the collimator between the aperture plates, through which the radiation could directly penetrate.

Another advantageous embodiment is distinguished by the fact that the second short side (the one further away from the borehole), is formed of two arcs, wherein one of the arcs is a quarter-circle having a diameter equal to the width of the aperture plate and a centerpoint midway between the long sides, and wherein the center of the other arc is located at the center of the bore hole. This special shape of the second short side ensures that at each angular setting, the cross-section required for absorption is already achieved at a short distance from the edge.

In order to simplify the construction of the setting mechanism, in another embodiment the first short side is in the shape of a semi-circle, whose center corresponds to the center of the bore hole. In this case, the setting mechanism is attached to the semi-circular short side.

A simpler construction of the setting mechanism, i.e., one without additional stopping devices, is achieved by having the setting mechanism comprise a worm gear drive for each of the aperture plates.

In another advantageous embodiment, the worm gear drive comprises a toothed sector created on the first, semicircular short side of each aperture plate and a worm gear that meshes with the toothed sector. This permits an exceptionally simple construction of the setting mechanism. Alternatively, the worm gears could be electrically driven by motors coupled either directly or by way of a belt transmission.

In another advantageous embodiment, each worm gear drive includes a hand wheel coupled for rotating the worm gear. By this means, the aperture plates can be individually adjusted in a simple manner.

An especially advantageous embodiment is distinguished by the fact that each aperture plate, when it is rotated inwards, extends into the aperture beyond the midpoint between the two axles. This method of design prevents scatter radiation from penetrating between aperture plates that are opposite to one another, when the aperture has been closed by the aperture plates.

Additional features and objects of the invention will be more readily appreciated and better understood by reference to the following detailed description which should be considered in conjunction with the drawings.

DESCRIPTION OF THE PREFERRED EMBODIMENT OF THE INVENTION

Figure 1:
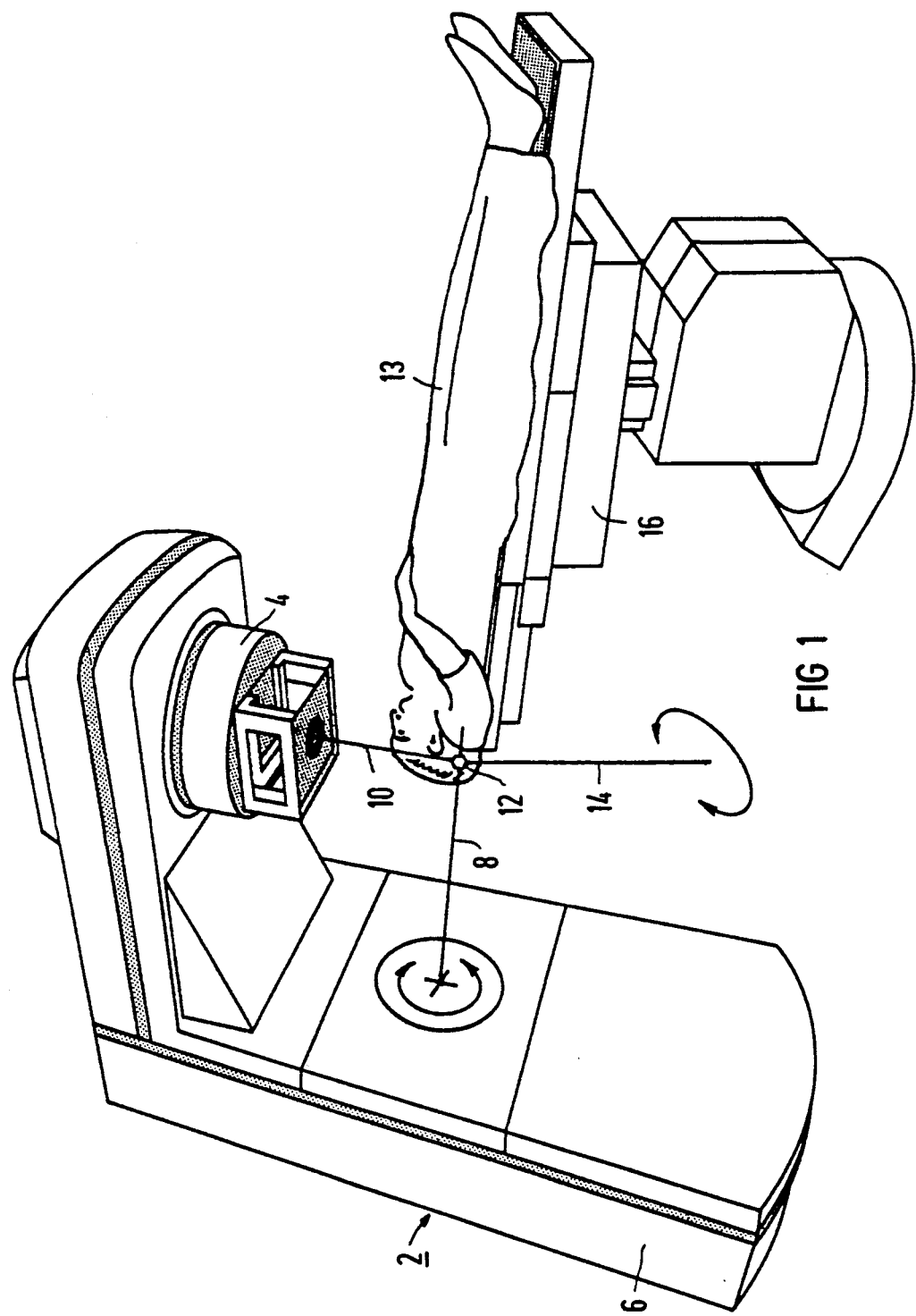
FIG. 1 shows a linear accelerator, with which a contour collimator in accordance with the invention is used.

FIG. 1 shows a part of a radiation therapy unit 2 of common design, in which a contour collimator 4 with rotating aperture plates constructed in accordance with the principles of the invention is used. The radiation therapy unit 2 comprises a gantry 6 which can be swiveled around a horizontal axis of rotation 8 in the course of a therapeutic treatment. The contour collimator 4 is fastened to a projection of the gantry 6. To generate the high-powered radiation required for the therapy, a linear accelerator is located in the radiation therapy unit 2. The main beam of the radiation bundle emitted from the linear accelerator 2 and the radiation therapy unit is designated by 10. Either electron radiation or photon radiation (gamma radiation) can be used for the therapy. During the treatment, the main beam 10 is trained on the zone 12 of a patient 13 which is to be treated and which lies in the isocenter of the gantry rotation. The rotational axis 8 of the gantry 6, the rotational axis 14 of a treatment table 16 and the beam axis 10 all intersect in the isocenter.

Figure 2:
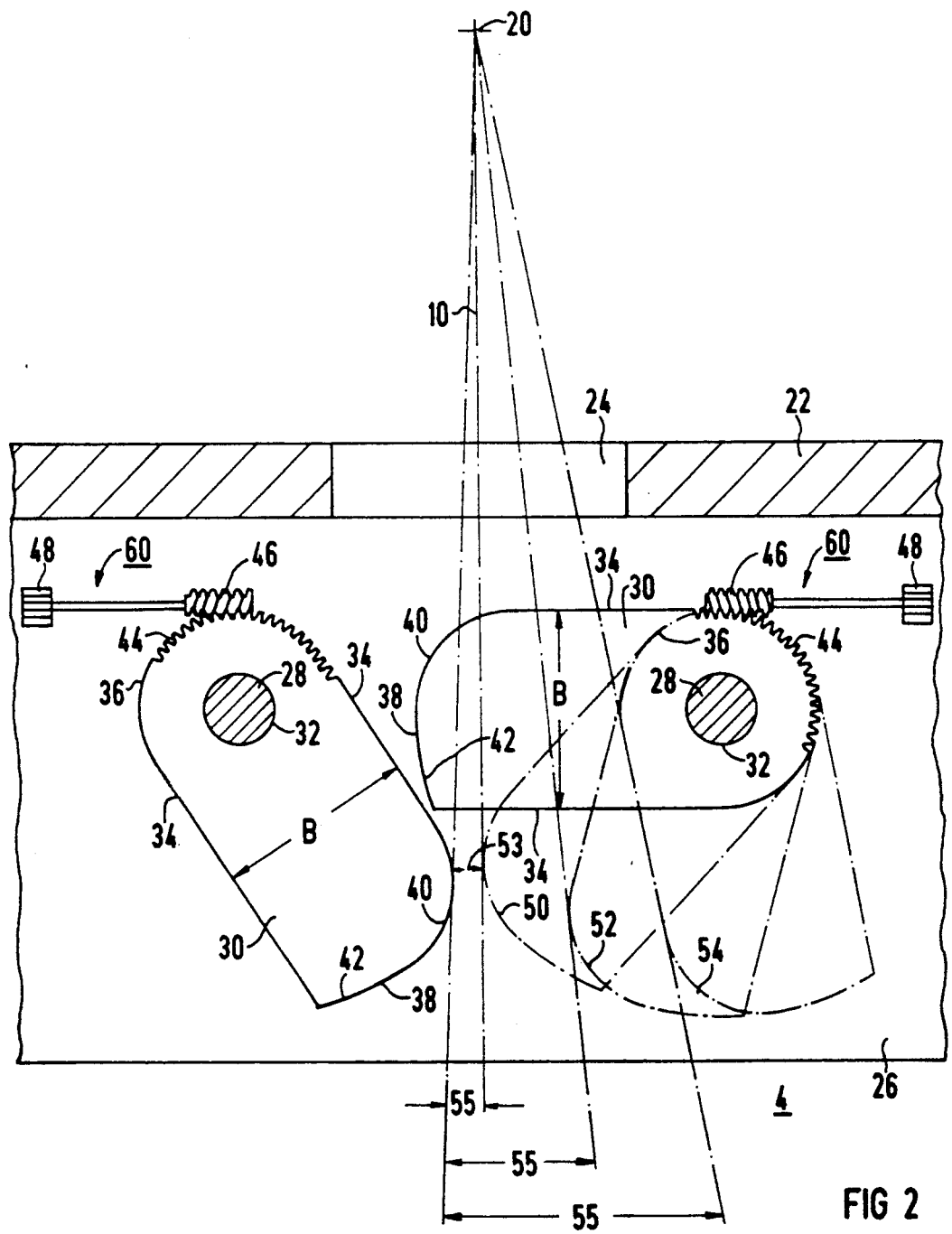
FIG. 2 shows a side view of a contour collimator with rotating aperture plates constructed in accordance with the principles of the invention.

FIG. 2 shows details of the collimator 4 in a lateral cross-section. For purposes of the description, it is assumed that the radiation travels in a vertical direction; the linear accelerator, as the source of radiation, is represented symbolically by the reference number 20. Starting from the radiation source 20, the contour collimator 4 comprises a round assembly plate 22, in the center of which is located a through-passage 24. Two side pieces 26 are fastened perpendicularly to the sides of the through-passage 24 to the assembly plate 22. In the cross-sectional presentation of FIG. 2, the rear side pieces 26 and the round assembly plate 22 are shown in part. The side pieces 26 consist of two rectangular plates. Between the two side pieces 26, two axles 28 are mounted parallel to the assembly plate 22 and perpendicular to the side pieces 26. On each axle 28 are arranged 13 aperture plates. For this purpose, a hole. 32 has been bored in each of the aperture plates 30.

Each aperture plate 30 has an elongated form that is bounded by two long sides 34 and a first and second short side, 36 and 38, respectively. The bore hole 32 is located in the vicinity of the first short side 36, midway between the two long sides 34. Each aperture plate 30 has a constant width B in its middle section.

The width B of the aperture plates 30 amounts to at least 76.2 mm or 3 inches. This width is sufficient to screen even high-powered gamma or photon radiation if the aperture plates are made of tungsten or tungsten alloy.

The short sides 36 and 38 of each aperture plate are rounded. While the first short side 36 is in the form of a semi-circle, the second short side 38 is made up of two arcs with different curvatures, 40 and 42. The two arcs 40 and 42 touch one another midway between the two long sides 34. The arc 40 is in the form of a quarter-circle, whose center lies midway between the two long sides 34. The center of the arc 42 is at the center of the borehole 32. As a result of the shaping of the second short side 38 as described above, the full cross section required to screen the beams is available at a short distance from the edge in every rotational position.

For the individual adjustment of the angle of rotation, each aperture plate 30 has on its first short side 36 a row of teeth 44, which interlocks with a worm gear 46. The worm gear 46 is connected to a hand wheel 48, by means of which the position of the rotating plates 30 can be set by hand.

In FIG. 2, various angles of rotation of the aperture plates 30 are indicated by the broken outlines 50, 52 and 54. Each aperture plate 30 can assume any desired angle of rotation within the area of rotation. The area of rotation is limited, on the one hand, by the horizontal position of the aperture 30 (in FIG. 2 the righthand aperture plate 30 is shown in this position) and, on the other, by the position indicated by the outline 54. If the aperture plate 30 takes the position indicated by the outline 54, the largest possible aperture 53 is created by the aperture plate 30. The aperture 53 created for the radiation by the aperture plates 30 is produced in FIG. 2 by the lefthand aperture plate 30 in conjunction with the positions of the righthand aperture plate 30 that are indicated by the outline 50, 52, 54. The irradiated field that is permitted by the aperture 53 is designated by 55, and increases as the distance from the radiation source 20 increases.

The closer the aperture 53 is to the zone 12 to be treated, the more sharply the field of irradiation is defined. For this reason, the aperture plates 30 can be rotated in the contour collimator 4 by the side furthest from the radiation souree 20 into the aperture 53. The aperture 53 is thereby kept close to the treatment zone 12; the unsharp area, that is, the area of the penumbra is kept small by this arrangement.

In the position of the left- and righthand aperture plates 30 shown in FIG. 2 by the solid lines, the aperture is closed. As a result of the overlapping, no undesired scatter radiation can occur between aperture plates 30 that are mounted opposite one another.

Figure 3:
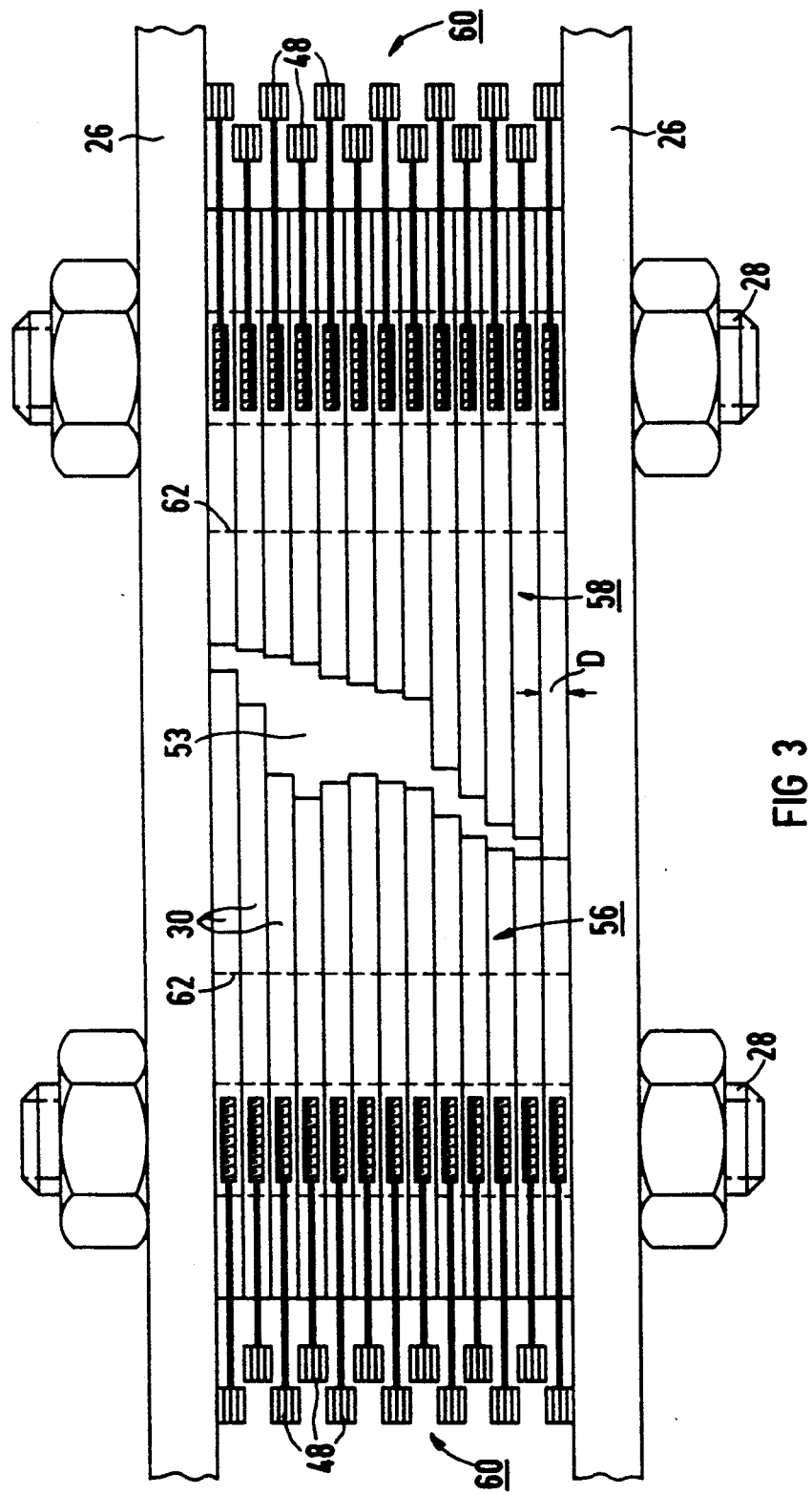
FIG. 3 shows a top view of the contour collimator according to FIG. 2.

FIG. 3 shows a top view, with the assembly plate 22 removed, of the two opposite stacks 56 and 58, in which the rotating plates 30 are arranged in each case on an axle 28. Each stack consists of 13 aperture plates 30. The stacks 56 and 58 ar arranged symmetrical to the main beam 10. The aperture plates 30 are all of a uniform thickness D. The uniform thickness D and an odd number of aperture plates 30 in a stack 56 or 58 prevent undesired scatter radiation, because there are no slits between the aperture plates 30 that are aligned at the radiation source, i.e. there is a solid plate aligned with the beam from the radiation source. By means of a setting mechanism 60, which comprises the worm drives 44, 46, 48 for each aperture plate 30, the individual aperture plates 30 are rotated into the aperture 53, in such a manner that the outline of the aperture 53 corresponds closely to the outline of the zone 12 that is to be treated. The maximum width of the aperture 53 created by the aperture plates 30 is determined by the distance between the axles 28 and the width of the aperture plates 30. The widest opening 53 is indicated by the broken lines 62 and is produced when all the aperture plates 30 are in the position 54 shown in FIG. 2. The maximum length of the aperture 53 is determined by the number of the aperture plates 30 and their thickness D. The thickness D of the aperture plates 30 also determines the accuracy with which an irregular outline of the treatment zone 12 can be duplicated by the aperture 53. It has been found that a thickness of the aperture plates amounting to 6.35 mm or ¼ inch is sufficient. The hand wheels 48 of the setting mechanism 60 are staggered in order to make them easier to operate.

There has thus been shown and described a contour collimator which fulfills all the objects and advantages sought for. Many changes, modifications, variations and other uses and applications of the subject invention will, however, become apparent to those skilled in the art after considering the specification and the accompanying drawings which disclose an embodiment thereof. All such changes, modifications, variations and other uses and applications which do not depart from the spirit and scope of the invention are deemed to be covered by the invention which is limited only by the claims which follow.

We claim:

1. A contour collimator, comprising:
two stacks of aperture plates rotatably mounted opposite to one another on respective opposed axles in a support means and creating an aperture between said opposed stacks of aperture plates;
a setting mechanism operatively connected to said aperture plates for individually rotating said aperture plates about said opposed axles and thereby altering said aperture created between said opposed stacks of aperture plates.

2. A contour collimator according to claim 1, wherein each aperture plate has an elongated shape and is bounded by two long sides and a first and second short side and wherein the vicinity of the first short side a hole is provided which receives a respective one of said axles.

3. A contour collimator according to claim 2, wherein each aperture plate has a constant width midsection and wherein said hole is located midway between said long sides.

4. A contour collimator according to claim 3, wherein the second short side, which is further away from said hole is formed by a first and a second arc, wherein the first arc is in the form of a quarter-circle with a diameter equal to the width of the aperture plate and whose center is located midway between the long sides, and wherein the center of the second arc is at the center of the hole.

5. A contour collimator according to claim 2, wherein the short sides of each aperture plate are rounded.

6. A contour collimator according to claim 2, wherein the first short side is in the form of a semicircle whose center is at the center of the hole and wherein the setting mechanism interacts with the semi-circular first short side.

7. A contour collimator according to claim 2, further including a worm gear drive comprising a toothed sector introduced on the first, semi-circular short side of each aperture plate and a worm gear that meshes with the toothing.

8. A contour collimator according to claim 1, wherein each aperture plate has a uniform thickness and wherein each stack has an odd number of aperture plates.

9. A contour collimator according to claim 1, wherein the setting mechanism comprises a worm gear drive provided for each aperture plate.

10. A contour collimator according to claim 9, wherein each worm drive comprises a hand wheel.

11. A contour collimator according to claim 1, wherein the aperture plates are made of tungsten.

12. A contour collimator according to claim 11, wherein the constant width of the aperture plates amounts to at least 76.2 mm or 3 inches.

13. A contour collimator according to claim 1, wherein each aperture plate, when rotated inwardly, extends into the aperture beyond the midpoint between the two axles.

* * * * *